(12) United States Patent
Dershem et al.

(10) Patent No.: US 7,285,613 B2
(45) Date of Patent: Oct. 23, 2007

(54) FREE-RADICAL CURABLE POLYESTERS AND METHODS FOR USE THEREOF

(75) Inventors: Stephen M. Dershem, San Diego, CA (US); Farhad G. Mizori, La Mesa, CA (US)

(73) Assignee: Designer Molecules, Inc., San Diego, CA (US)

( * ) Notice: Subject to any disclaimer, the term of this patent is extended or adjusted under 35 U.S.C. 154(b) by 0 days.

(21) Appl. No.: 11/145,382

(22) Filed: Jun. 3, 2005

(65) Prior Publication Data

US 2005/0272888 A1 Dec. 8, 2005

Related U.S. Application Data

(60) Provisional application No. 60/655,709, filed on Feb. 23, 2005, provisional application No. 60/577,004, filed on Jun. 4, 2004.

(51) Int. Cl.
- *C08F 4/80* (2006.01)
- *C07C 69/76* (2006.01)
- *C07C 69/74* (2006.01)

(52) U.S. Cl. ............ 526/285; 526/319; 526/346; 526/313; 560/90; 560/121; 560/122; 560/127

(58) Field of Classification Search ........ 526/285, 526/72, 319, 346, 313; 560/90, 121, 122, 560/127
See application file for complete search history.

(56) References Cited

U.S. PATENT DOCUMENTS

| | | | | |
|---|---|---|---|---|
| 3,918,393 A | * | 11/1975 | Hahn | ............ 427/494 |
| 4,363,907 A | * | 12/1982 | Hefner et al. | ............ 528/287 |
| 4,540,829 A | * | 9/1985 | Hefner, Jr. | ............ 568/634 |
| 4,560,768 A | * | 12/1985 | Hefner et al. | ............ 548/435 |
| 4,623,696 A | * | 11/1986 | Mabrey et al. | ............ 525/33 |
| 4,753,982 A | * | 6/1988 | Hefner, Jr. | ............ 525/31 |
| 4,777,209 A | * | 10/1988 | Hefner, Jr. | ............ 525/28 |
| 5,437,964 A | * | 8/1995 | Lapin et al. | ............ 430/280.1 |
| 5,973,166 A | | 10/1999 | Mizori | |
| 6,034,194 A | | 3/2000 | Dershem | |
| 6,034,195 A | | 3/2000 | Dershem | |
| 6,063,828 A | | 5/2000 | Ma | |
| 6,187,886 B1 | | 2/2001 | Husson, Jr. | |
| 6,265,530 B1 | | 7/2001 | Herr | |
| 6,281,314 B1 | | 8/2001 | Tong | |
| 6,316,566 B1 | | 11/2001 | Ma | |
| 6,355,750 B1 | | 3/2002 | Herr | |
| 6,699,929 B2 | | 3/2004 | Musa | |
| 6,790,597 B2 | | 9/2004 | Dershem | |
| 6,825,245 B2 | | 11/2004 | Dershem | |
| 6,831,132 B2 | | 12/2004 | Liu | |
| 6,852,814 B2 | | 2/2005 | Dershem | |
| 6,916,856 B2 | | 7/2005 | Dershem | |
| 2003/0129438 A1 | * | 7/2003 | Becker et al. | ............ 428/620 |

FOREIGN PATENT DOCUMENTS

JP  2004037475 A  *  2/2004

* cited by examiner

*Primary Examiner*—David W. Wu
*Assistant Examiner*—M. Bernshteyn
(74) *Attorney, Agent, or Firm*—Kevin J. Forrestal

(57) ABSTRACT

The invention is based on the discovery that certain polyester compounds bearing free-radical curable moieties are useful as b-stageable adhesives for the microelectonic packaging industry.

6 Claims, No Drawings

FREE-RADICAL CURABLE POLYESTERS AND METHODS FOR USE THEREOF

RELATED APPLICATIONS

This application claims the benefit of priority of U.S. Provisional Application Ser. No. 60/577,004 filed Jun. 4, 2004, and U.S. Provisional Application Ser. No. 60/655,709 filed Feb. 23, 2005, the entire disclosures of which are incorporated herein by reference.

FIELD OF THE INVENTION

The present invention relates to thermosetting adhesive compositions, methods of preparation and uses therefor. In particular, the present invention relates to thermosetting compounds and compositions containing free radical curable polyester compounds.

BACKGROUND OF THE INVENTION

Adhesive compositions, particularly conductive adhesives, are used for a variety of purposes in the fabrication and assembly of semiconductor packages and microelectronic devices. The more prominent uses include bonding of electronic elements such as integrated circuit chips to lead frames or other substrates, and bonding of circuit packages or assemblies to printed wire boards. Adhesives useful for electronic packaging applications typically exhibit properties such as good mechanical strength, curing properties that do not affect the component or the carrier, and thixotropic properties compatible with application to microelectronic and semiconductor components.

Recently, there has been an increased interest in b-stageable adhesives. A b-stageable material is actually a thermosetting material that has a first solid phase followed by a rubbery stage at elevated temperature, followed by yet another solid phase at an even higher temperature. The transition from the rubbery stage to the second solid phase is known as thermosetting. However, prior to that, the material behaves similarly to a thermoplastic material. Thus, such a material would permit low lamination temperatures while providing high thermal stability. In addition, b-stageable adhesives eliminate many of the storage, handling, dispensing, and processing issues that exist when dispensing an adhesive in a flowable form. Accordingly, there is a continuing need for b-stageable adhesives in the electronic packaging industry.

SUMMARY OF THE INVENTION

The invention is based on the discovery that a certain polyester compounds are useful as adhesives for the microelectronic packaging industry. In certain embodiments, the adhesives described herein are b-stageable adhesives. In one embodiment of the invention there are provided compounds having the structure I:

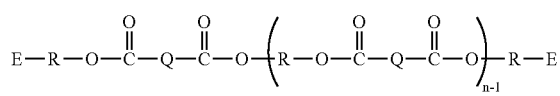

wherein:
R and Q are each independently substituted or unsubstituted aliphatic, aryl, or heteroaryl;
each E is independently acrylate, methacrylate, maleimide, styrenic, vinyl ester, olefin, allyl, vinyl ether, itaconate, or fumarate; and n is 1 to about 10.

In another embodiment, there are provided adhesive compositions including at least one of the above described compounds, and at least one curing initiator.

In yet another embodiment, there are provided b-stageable die-attach pastes including
a) 2 weight percent to about 98 weight percent (wt %) of at least one of the above-described compounds, or combinations thereof, based on total weight of the composition,
b) 0 to about 90 wt % of a conductive filler;
d) 0.1 wt % to about 5 wt % of at least one curing initiator, based on total weight of the composition;
e) 0.1 wt % to about 4 wt %, of at least one coupling agent, based on total weight of the composition.

In another embodiment, there are provided assemblies including a first article permanently adhered to a second article by a cured aliquot of the die-attach pastes according to the invention.

In another embodiment, there are provided methods for adhesively attaching a first article to a second article. Such methods can be performed, for example, by
(a) applying an aliquot of the adhesive composition of the invention to the first article,
(b) bringing the first and second article into intimate contact to form an assembly wherein the first article and the second article are separated only by the adhesive composition applied in (a), and thereafter,
(c) subjecting the assembly to conditions suitable to cure the adhesive composition.

In another embodiment, there are provided methods for adhesively attaching a semiconductor die to a substrate. Such methods can be performed, for example, by
(a) applying the die attach paste of the invention to the substrate and/or the microelectronic device,
(b) subjecting the substrate and/or the microelectronic device to conditions suitable to form a b-staged the curable film,
(c) exposing the b-staged curable film to temperature conditions suitable to melt the film,
(d) bringing the substrate and the device into intimate contact to form an assembly wherein the substrate and the device are separated only by the die-attach paste, and
(e) subjecting the b-staged curable film to conditions suitable to cure the melted film.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting.

The section headings used herein are for organizational purposes only and are not to be construed as limiting the subject matter described.

Definitions

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

As used herein, "aliphatic" refers to any alkyl, alkenyl, or cycloalkyl moiety.

As used herein, "alkyl" refers to straight or branched chain hydrocarbyl groups having from 1 up to about 100 carbon atoms. "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, amido, —C(O)H, —C(O)—, —C(O)—, —S—, —S(O)$_2$, —OC(O)—O—, —NR—C(O), —NR—C(O)—NR, —OC(O)—NR, wherein R is H or lower alkyl, acyl, oxyacyl, carboxyl, carbamate, sulfonyl, sulfonamide, sulfuryl, and the like.

As used herein, "cycloalkyl" refers to cyclic ring-containing groups containing in the range of about 5 up to about 20 carbon atoms, and "substituted cycloalkyl" refers to cycloalkyl groups further bearing one or more substituents as set forth above. In some embodiments, the cycloalkyl refers to cyclic ring-containing groups containing in the range of about 5 up to about 12 carbon atoms As used herein, "aryl" refers to aromatic groups having in the range of 6 up to 14 carbon atoms and "substituted aryl" refers to aryl groups further bearing one or more substituents as set forth above.

As used herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above. The term "heterocyclic" is also intended to refer to heteroaryl moieties.

As used herein, "alkenyl" refers to straight or branched chain hydrocarbyl groups having at least one carbon-carbon double bond, and having in the range of about 2 up to 100 carbon atoms, and "substituted alkenyl" refers to alkenyl groups further bearing one or more substituents as set forth above.

As used herein, the term "acrylate" refers to a compound bearing at least one moiety having the structure:

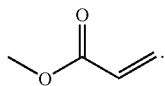

As used herein, the term "methacrylate" refers to a compound bearing at least one moiety having the structure:

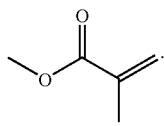

As used herein, the term "maleimide" refers to a compound bearing at least one moiety having the structure:

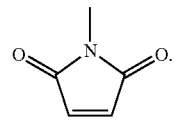

As used herein, the term "epoxy" refers to a compound bearing at least one moiety having the structure:

As used herein, the term "vinyl ether" refers to a compound bearing at least one moiety having the structure:

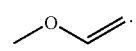

As used herein, the term "acrylamide" refers to a compound bearing at least one moiety having the structure:

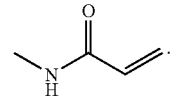

As used herein, the term "methacrylamide" refers to a compound bearing at least one moiety having the structure:

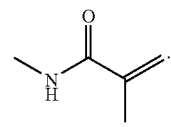

The invention is based on the discovery that certain polyester compounds are useful as adhesives for the microelectronic packaging industry. In certain embodiments, the adhesives described herein are b-stageable adhesives. In one embodiment of the invention there are provided compounds having the structure I:

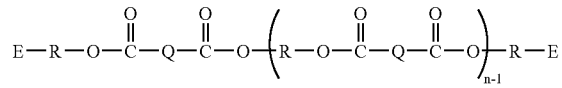

wherein:
R and Q are each independently substituted or unsubstituted aliphatic, aryl, or heteroaryl;
each E is independently acrylate, methacrylate, maleimide, styrenic, vinyl ester, olefin, allyl, vinyl ether, itaconate, or fumarate; and
n is 1 to about 10.

In certain embodiments, R is a substituted or unsubstituted cycloalkyl having from 5 to about 20 carbon atoms. In other embodiments, R is a substituted or unsubstituted cycloalkyl having from 5 to about 12 carbon atoms. In some embodiments, R is a substituted or unsubstituted cyclopentyl, cyclohexyl, norbornyl, tetracyclododecyl, or dicyclopentadienyl.

A wide variety of aryl and heteroaryl moieties are contemplated for Q in the practice of the invention. In some embodiments, Q is a substituted or unsubstituted aryl or heteroaryl having from 6 to about 14 carbon atoms. In other embodiments, Q is a substituted or unsubstituted phenyl or naphthyl. In further embodiments, Q is a substituted or unsubstituted cycloalkyl, such as, for example, norbornyl.

It is understood that a wide variety of polyester compounds are contemplated for use in the practice of the invention. In one embodiment of the invention, the polyester compounds contain acrylate or methacrylate moieties. Some examples of this embodiment are set forth below:

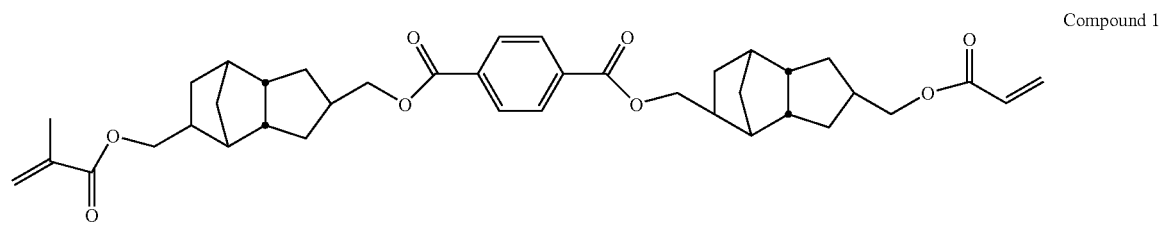

Compound 1

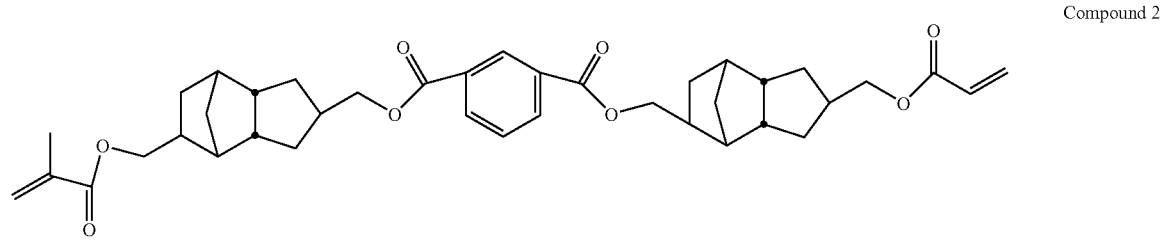

Compound 2

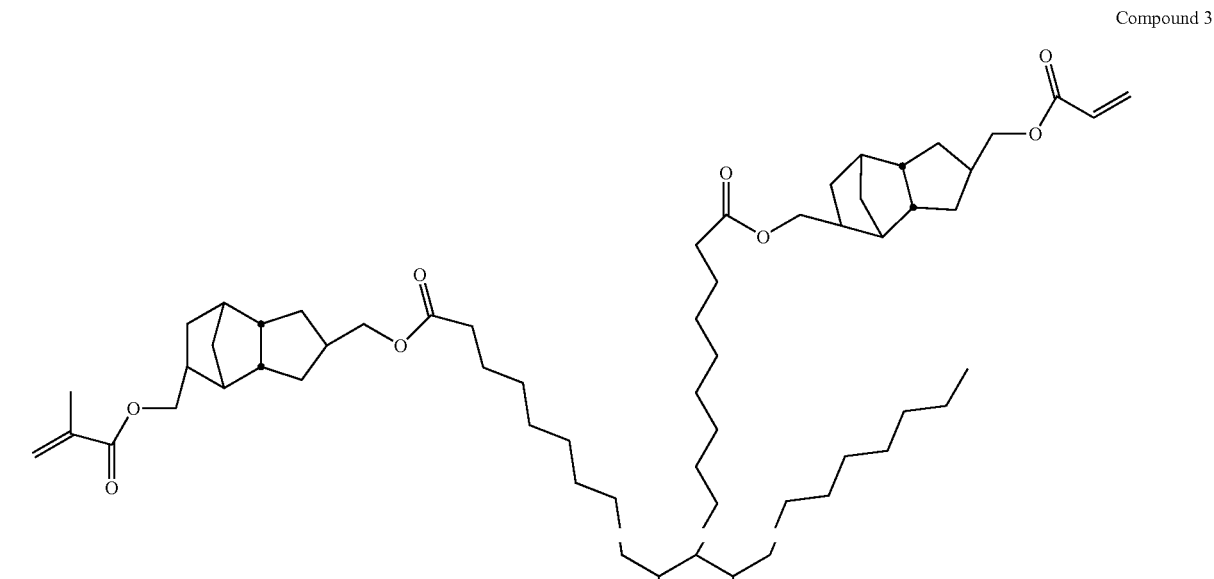

Compound 3

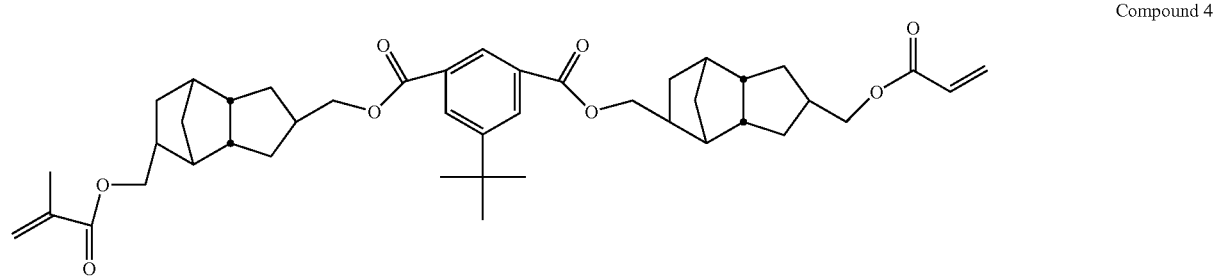

Compound 4

-continued
Compound 5
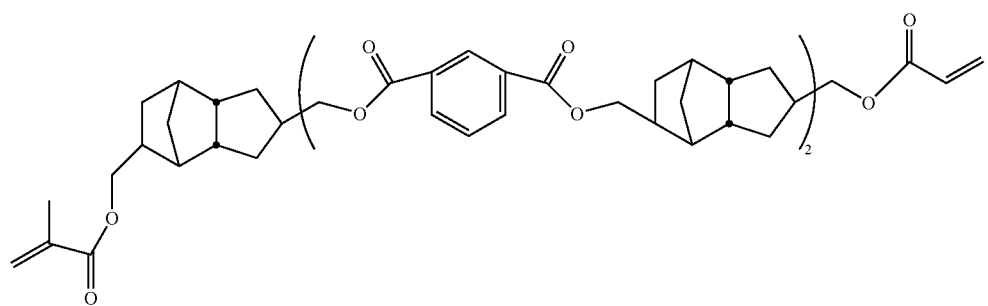
Compound 6
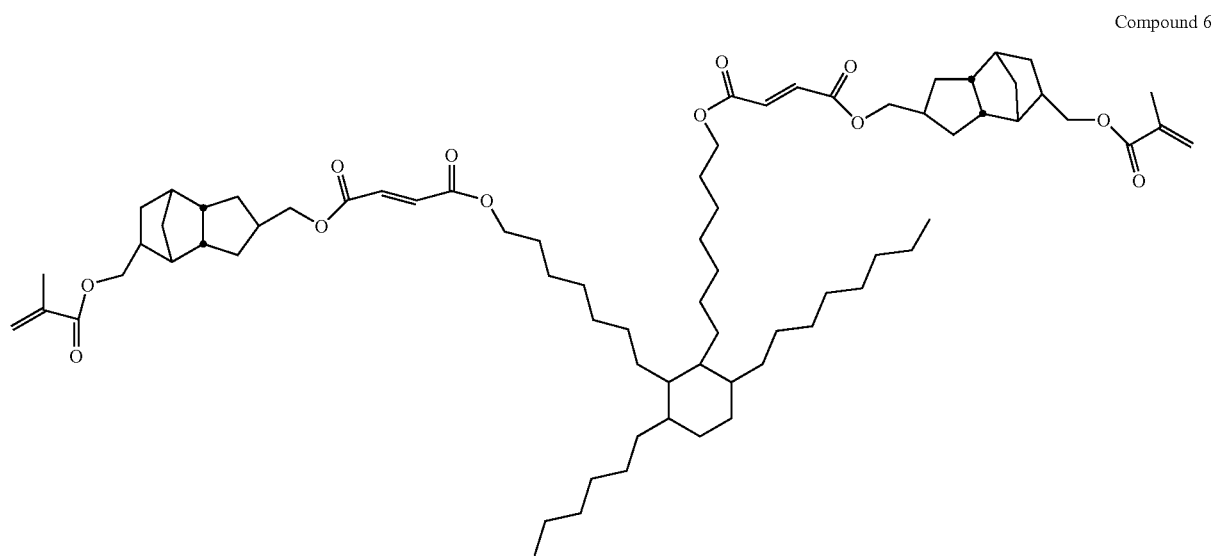
Compound 7
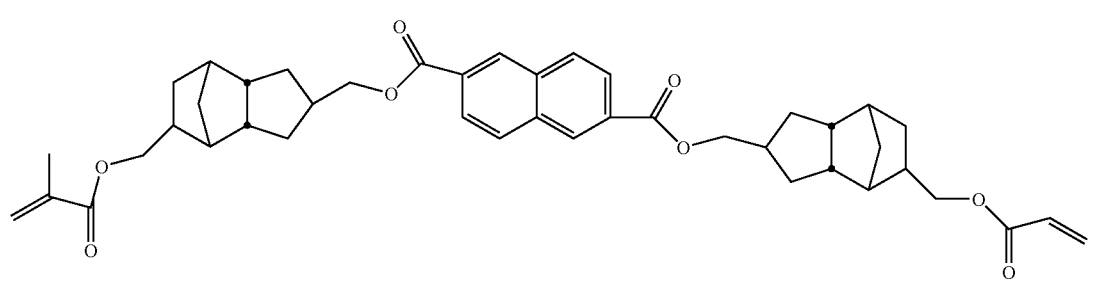
Compound 8
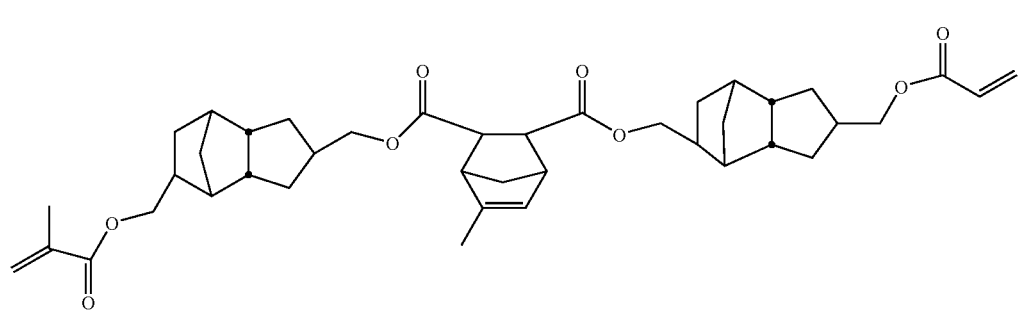

-continued
Compound 9
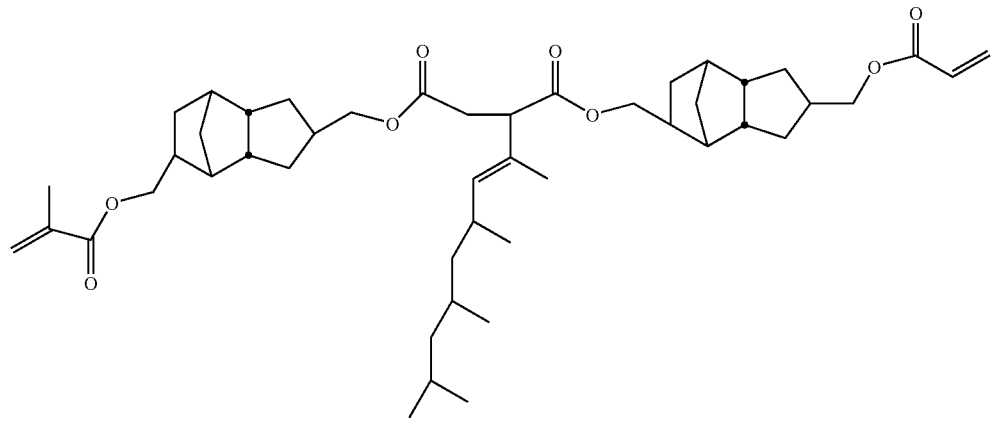
Compound 10
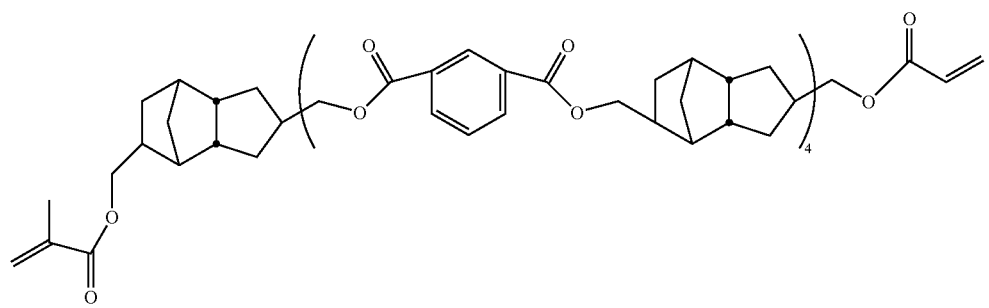
Compound 11
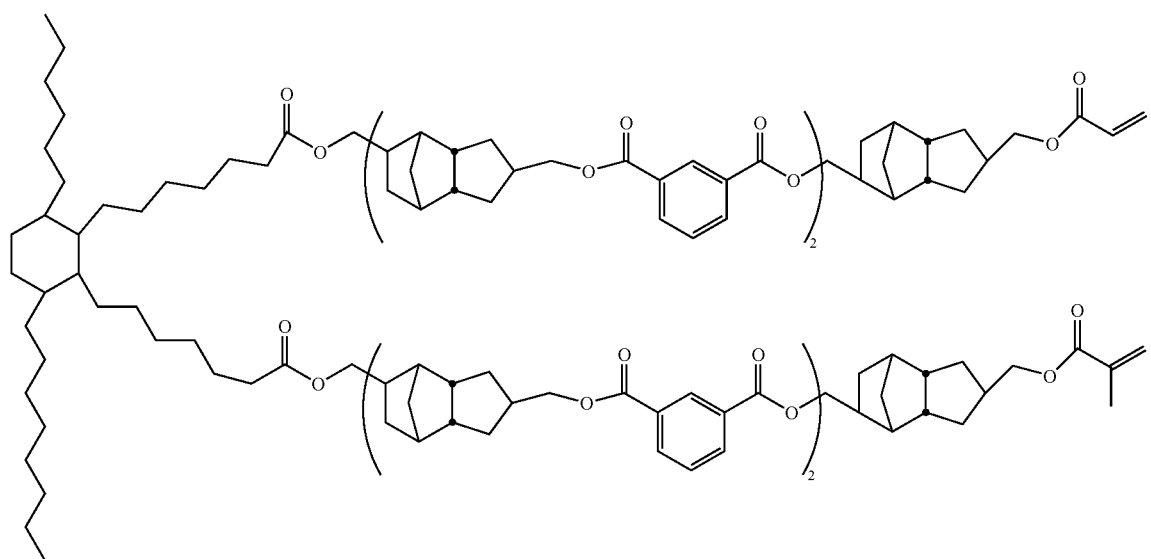

-continued
Compound 12
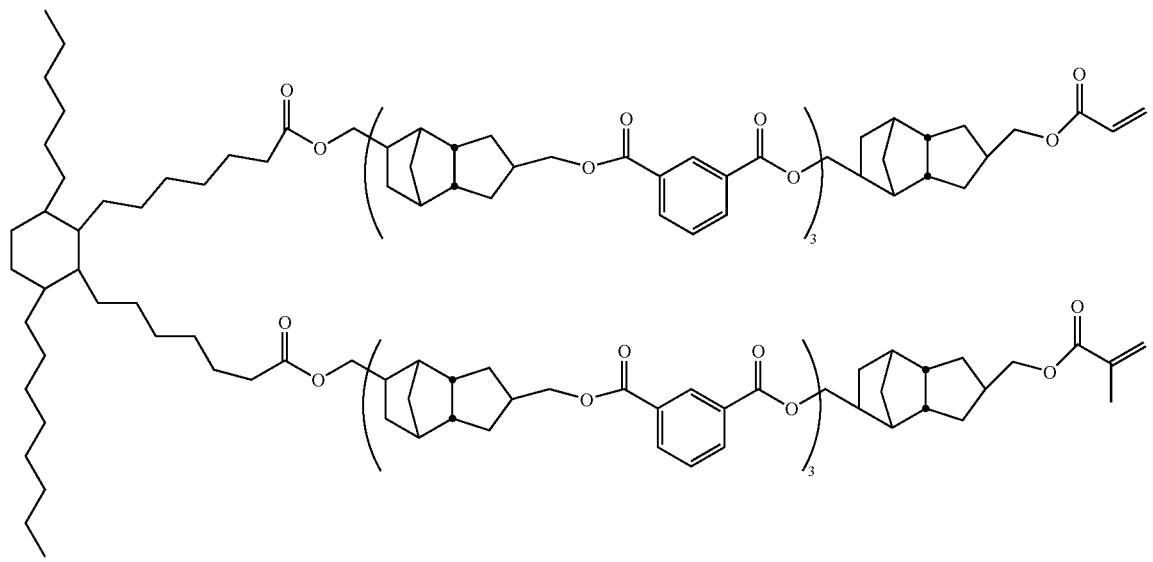
Compound 13
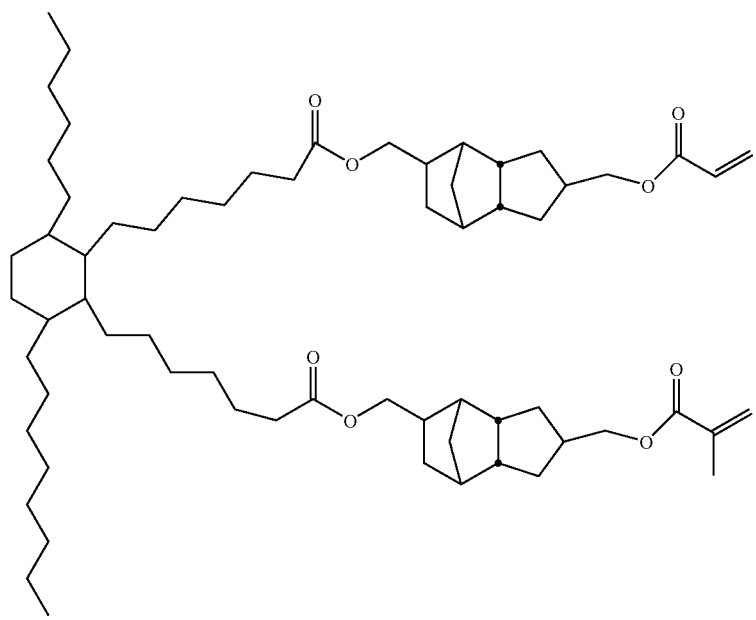
Compound 14
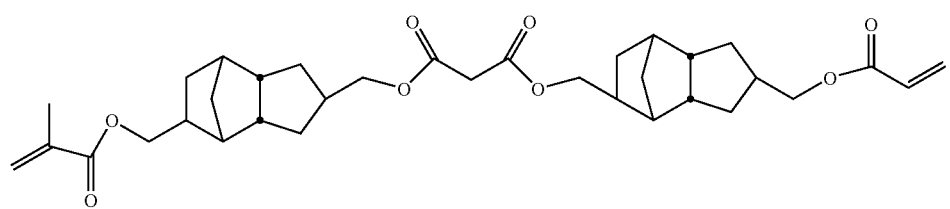
Compound 15
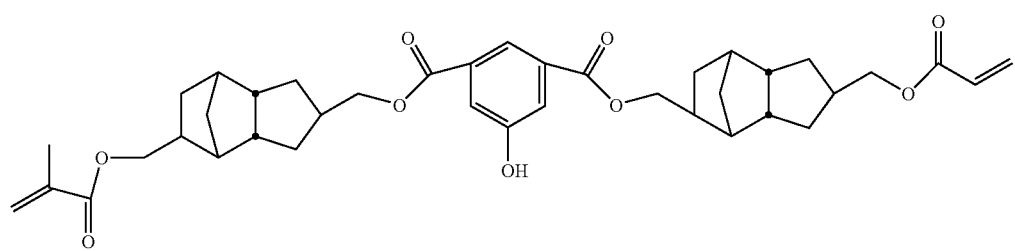

-continued
Compound 15
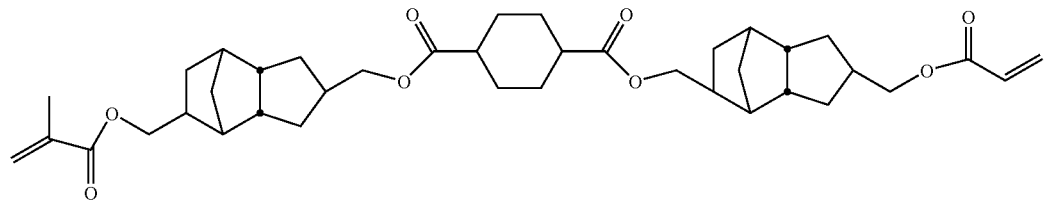
Compound 16
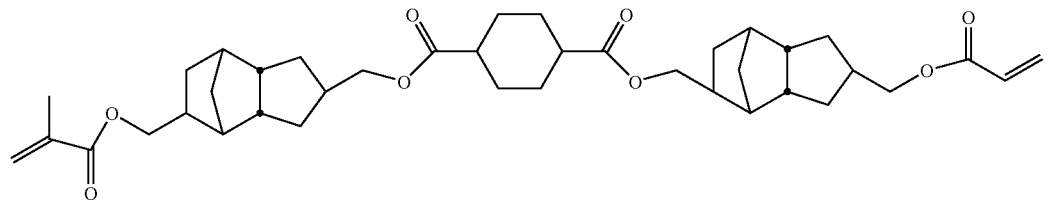
Compound 17
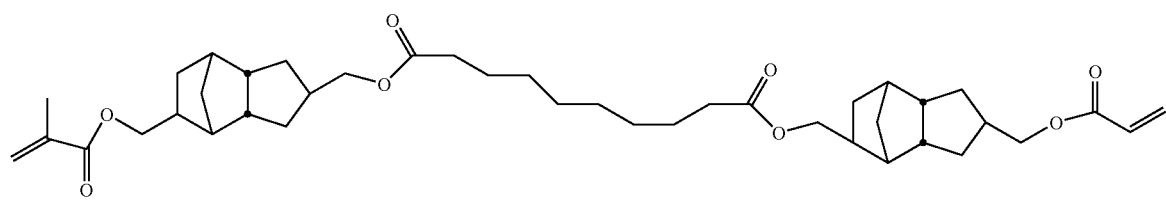
Compound 18
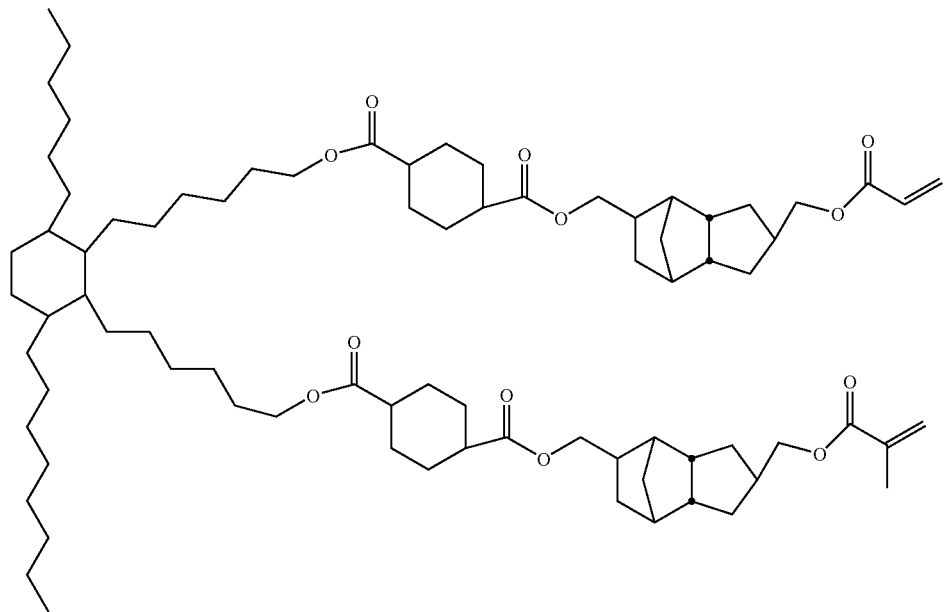

-continued
Compound 19
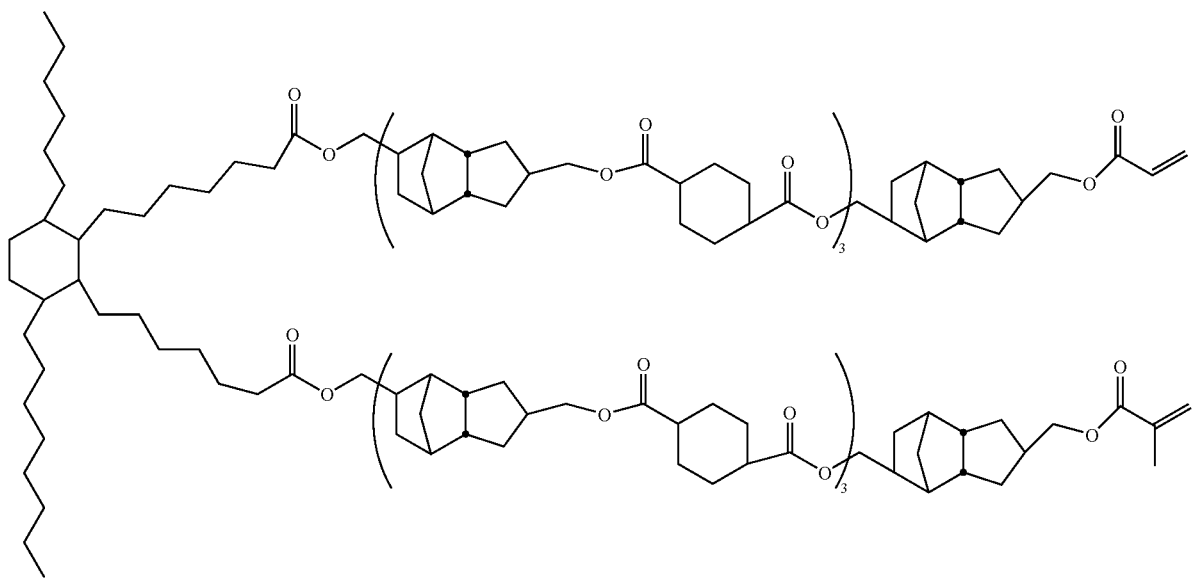
Compound 20
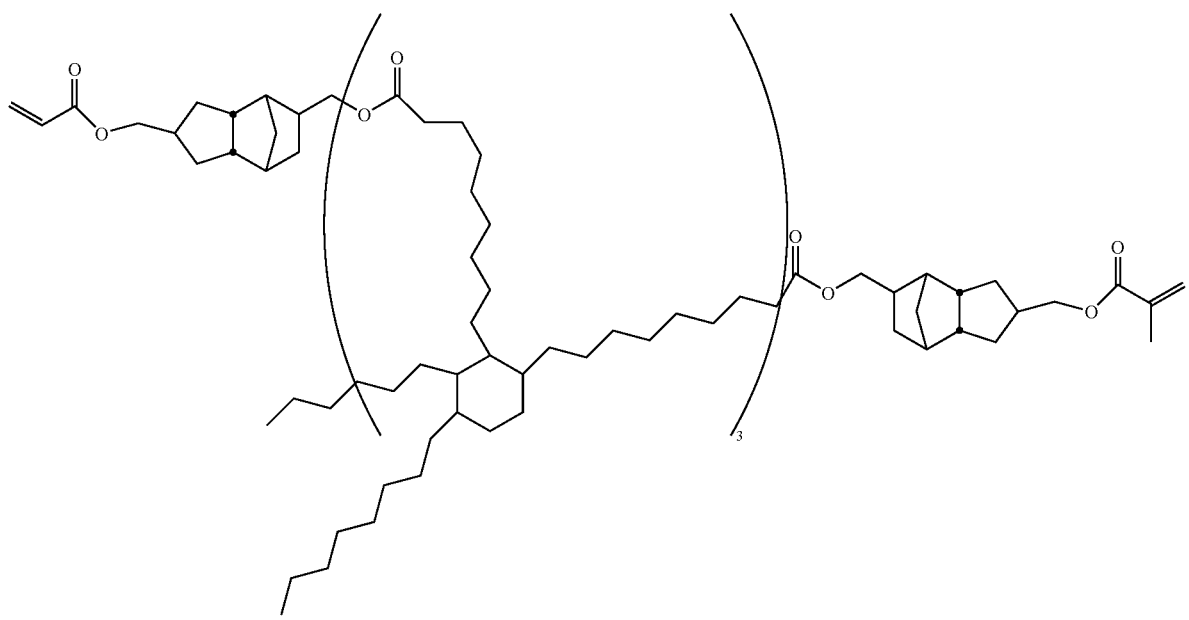

-continued

Compound 21

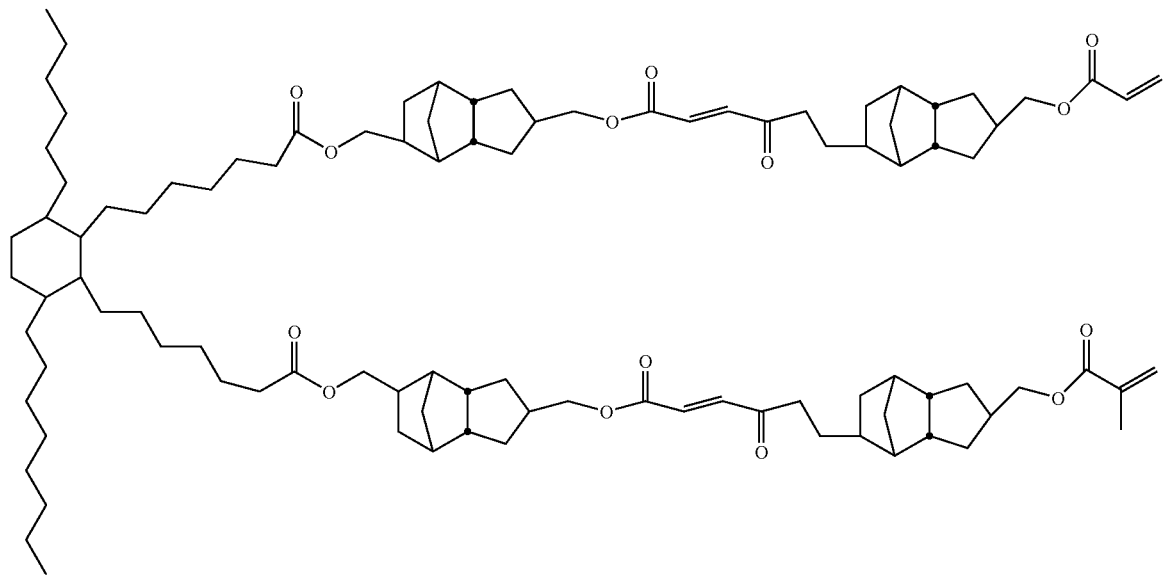

The compounds of the invention are readily prepared according to organic chemistry techniques well-known to those skilled in the art. For example, the esters described herein are typically prepared by conversion of the acid to the corresponding ester under acid or base catalysis.

The polyester compounds of the invention may be used independently in adhesive compositions, or may be combined with other adhesive compounds and resins. In one embodiment, a polyester compound of the invention may be used as the sole thermoset monomer of the adhesive composition. In another embodiment, the polyester compound of the invention may be combined with other thermoset monomers to make a fully formulated adhesive.

In one embodiment, there is provided an adhesive composition including at least one polyester compound of the invention and at least one curing initiator.

In some embodiments, the polyester compound is present in the composition from 2 weight percent to about 98 weight percent (wt %) based on total weight of the composition. In other embodiments, there is at least one co-monomer typically present in the composition from 10 wt % to about 90 wt % based on total weight of the composition. Such comonomers include, for example, acrylates, methacrylates, maleimides, vinyl ethers, vinyl esters, styrenic compounds, allyl functional compounds, olefins, and the like;

The at least one curing initiator is typically present in the composition from 0.1 wt % to about 5 wt % based on total weight of the composition, and is typically a free-radical initiator. As used herein, the term "free radical initiator" refers to any chemical species which, upon exposure to sufficient energy (e.g., light, heat, or the like), decomposes into two parts which are uncharged, but which each possess at least one unpaired electron. Preferred free radical initiators contemplated for use in the practice of the present invention are compounds which decompose (i.e., have a half life in the range of about 10 hours) at temperatures in the range of about 70° C. up to 180° C. Exemplary free radical initiators contemplated for use in the practice of the present invention include peroxides (e.g., dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis(tert-butyl peroxyisopropyl)benzene, and tert-butyl hydroperoxide), azo compounds (e.g., 2,2'-azobis(2-methyl-propanenitrile), 2,2'-azobis(2-methylbutanenitrile), and 1,1'-azobis(cyclohexanecarbonitrile)), and the like.

The term "free radical initiator" also includes photoinitiators. For example, for invention adhesive compositions that contain a photoinitiator, the curing process can be initiated by UV radiation. In one embodiment, the photoinitiator is present at a concentration of 0.1 wt % to 5 wt % based on the total weight of the organic compounds in the composition (excluding any filler). In a one embodiment, the photoinitiator comprises 0.1 wt % to 3.0 wt %, based on the total weight of the organic compounds in the composition. Photoinitiators include benzoin derivatives, benzilketals, α,α-dialkoxyacetophenones, α-hydroxyalkylphenones, α-aminoalkylphenones, acylphosphine oxides, titanocene compounds, combinations of benzophenones and amines or Michler's ketone, and the like.

In another embodiment of the invention, there are provided die-attach pastes including 2 weight percent to about 98 weight percent (wt %) of at least one polyester compound described herein, or combinations thereof, based on total weight of the composition; optionally, 10 wt % to about 90 wt % of at least one additional compound selected from the group consisting of acrylates, methacrylates, maleimides, vinyl ethers, vinyl esters, styrenic compounds, olefins, allyl functional compounds, and the like, based on total weight of the composition; 0 to about 90 wt % of a conductive filler; 0.1 wt % to about 5 wt % of at least one curing initiator, based on total weight of the composition; and 0.1 wt % to about 4 wt %, of at least one coupling agent, based on total weight of the composition. In some embodiments, the additional compound includes, for example, epoxies (such as phenolics, novalacs (both phenolic and cresolic) and the like), imides, monomaleimides, bismaleimides, polymaleimides, cyanate esters, vinyl ethers, vinyl esters, vinyl acetates, esters, ureas, amides, olefins (such as ethylenes, propylenes, and the like) siloxanes, cyanoacrylates, styrenes, and the like, or combinations thereof.

In one embodiment, there is provided a b-stageable die-attach paste including:

a) 2 weight percent to about 98 weight percent (wt %) based on total weight of the composition, of a polyester compound having the structure I:

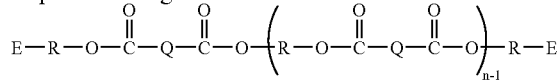

wherein:
R and Q are each independently substituted or unsubstituted aliphatic, aryl, or heteroaryl;
each E is independently acrylate, methacrylate, maleimide, styrenic, vinyl ester, olefin, allyl, vinyl ether, itaconate, or fumarate; and
n is 1 to about 10;

b) 0 to about 90 wt % of a filler;

d) 0.1 wt % to about 5 wt % of at least one curing initiator, based on total weight of the composition;

e) 0.1 wt % to about 4 wt %, of at least one coupling agent, based on total weight of the composition.

As used herein, "b-stageable" means that the adhesive has a first solid phase followed by a rubbery stage at elevated temperature, followed by yet another solid phase at an even higher temperature. The transition from the rubbery stage to the second solid phase is thermosetting. However, prior to that, the material behaves similarly to a thermoplastic material. Thus, such an adhesive allows for low lamination temperatures while providing high thermal stability.

The b-stageable adhesive can be dispensed onto a die or a substrate by a variety of methods well known to those skilled in the art. In some embodiments, the adhesive is cast from solution using techniques such as spin coating, spray coating, stencil printing, screen printing, and the like.

In certain embodiments, the choice of solvent or solvent system may play an important role in the dispensing characteristics of the b-stageable adhesive. For example, when the b-stageable adhesive is spin coated onto a circular wafer, it is desirable to have an even coating throughout the entire wafer, i.e., the solvent or solvent system should have the ability to deliver the same amount of adhesive to each point on the wafer. Thus, the adhesive will be evenly coated throughout, i.e., there will be the same amount of material at the center of the wafer as at the edges. Ideally, the adhesive is "Newtonian", with a slope of 1.0. In certain embodiments, the solvent or solvent systems used to dispense the b-stageable adhesive have slopes ranging from 1.0 to about 1.2.

In some instances, the b-stageable adhesive is dispensed onto a die that has been coated with a polyimide. Thus, the solvent or solvent system used to dispense the b-stageable adhesive should not have any deleterious effects on the polyimide coating. To achieve this goal, in certain embodiments, the solvent system will include a polar solvent in combination with a nonpolar solvent. Typically, the polar solvent is a good solvent for the polyester compound used as the b-stageable adhesive, and the nonpolar solvent is a non-solvent for the polyester compound. In addition, the polar solvent typically has a lower boiling point than the non-polar solvent. Without wishing to be bound by theory, it is believed that when the adhesive is dispensed and then b-staged, the lower boiling polar solvent escapes first, leaving behind only the nonpolar non-solvent, essentially precipitating the polymer uniformly and leaving the polyimide film undamaged.

In some embodiments, the solvent or solvent system has a boiling point ranging from about 150° C. up to about 300° C. In some embodiments, the solvent system is a combination of dimethyl phthalate (DMP), NOPAR 13, and terpineol. In other embodiments, the solvent system is a 1:1 (by volume) ratio of terpineol and NOPAR 13.

Fillers contemplated for use in the practice of the present invention can be electrically conductive and/or thermally conductive, and/or fillers which act primarily to modify the rheology of the resulting composition. Examples of suitable electrically conductive fillers which can be employed in the practice of the present invention include silver, nickel, copper, aluminum, palladium, gold, graphite, metal-coated graphite (e.g., nickel-coated graphite, copper-coated graphite, and the like), and the like. Examples of suitable thermally conductive fillers which can be employed in the practice of the present invention include graphite, aluminum nitride, silicon carbide, boron nitride, diamond dust, alumina, and the like. Compounds which act primarily to modify rheology include polysiloxanes (such as polydimethyl siloxanes) silica, fumed silica, alumina, titania, and the like.

As used herein, the term "coupling agent" refers to chemical species that are capable of bonding to a mineral surface and which also contain polymerizably reactive functional group(s) so as to enable interaction with the adhesive composition. Coupling agents thus facilitate linkage of the die-attach paste to the substrate to which it is applied.

Exemplary coupling agents contemplated for use in the practice of the present invention include silicate esters, metal acrylate salts (e.g., aluminum methacrylate), titanates (e.g., titanium methacryloxyethylacetoacetate triisopropoxide), or compounds that contain a copolymerizable group and a chelating ligand (e.g., phosphine, mercaptan, acetoacetate, and the like). In some embodiments, the coupling agents contain both a co-polymerizable function (e.g., vinyl moiety, acrylate moiety, methacrylate moiety, and the like), as well as a silicate ester function. The silicate ester portion of the coupling agent is capable of condensing with metal hydroxides present on the mineral surface of substrate, while the co-polymerizable function is capable of co-polymerizing with the other reactive components of invention die-attach paste. In certain embodiments coupling agents contemplated for use in the practice of the invention are oligomeric silicate coupling agents such as poly(methoxyvinylsiloxane).

In some embodiments, both photoinitiation and thermal initiation may be desirable. For example, curing of a photoinitiator-containing adhesive can be started by UV irradiation, and in a later processing step, curing can be completed by the application of heat to accomplish a free-radical cure. Both UV and thermal initiators may therefore be added to the adhesive composition.

In general, these b-stageable compositions will cure within a temperature range of 80-220° C., and curing will be effected within a length of time of less than 1 minute to 60 minutes. The b-stageable die-attach paste may be preapplied onto either a semiconductor die or onto a substrate. As will be understood by those skilled in the art, the time and temperature curing profile for each adhesive composition will vary, and different compositions can be designed to provide the curing profile that will be suited to the particular industrial manufacturing process.

In certain embodiments, the adhesive compositions may contain compounds that lend additional flexibility and toughness to the resultant cured adhesive. Such compounds may be any thermoset or thermoplastic material having a Tg of 50° C. or less, and typically will be a polymeric material characterized by free rotation about the chemical bonds, the presence of ether groups, and the absence of ring structures. Suitable such modifiers include polyacrylates, poly(butadiene), polyTHF (polymerized tetrahydrofuran, also known as poly(1,4-butanediol)), CTBN (carboxy-terminated butadiene-acrylonitrile) rubber, and polypropylene glycol. When present, toughening compounds may be in an amount up to about 15 percent by weight of the maleimide and other monofunctional vinyl compound.

Inhibitors for free-radial cure may also be added to the adhesive compositions and die-attach pastes described herein to extend the useful shelf life of compositions containing the polyester linked acrylates and methacrylates. Examples of these inhibitors include hindered phenols such as 2,6-di-tert-butyl-4-methylphenol; 2,6-di-tert-butyl-4-methoxyphenol; tert-butyl hydroquinone; tetrakis(methylene(3,5-di-tert-butyl-4-hydroxyhydrocinnamate))benzene; 2,2'-methylenebis(6-tert-butyl-p-cresol); and 1,3,5-trimethyl-2,4,6-tris(3',5'-di-tert-butyl-4-hydroxybenzyl)benzene. Other useful hydrogen-donating antioxidants include derivatives of p-phenylenediamine and diphenylamine. It is also well know in the art that hydrogen-donating antioxidants may be synergistically combined with quinones, and metal deactivators to make a very efficient inhibitor package. Examples of suitable quinones include benzoquinone, 2-tert butyl- 1,4-benzoquinone; 2-phenyl-1,4-benzoquinone; naphthoquinone, and 2,5-dichloro-1,4-benzoquinone. Examples of metal deactivators include N,N'-bis(3,5-di-tert-butyl-4-hydroxyhydrocinnamoyl)hydrazine; oxalyl bis(benzylidenehydrazide); and N-phenyl-N'-(4-toluenesulfonyl)-p-phenylenediamine. Nitroxyl radical compounds such as TEMPO (2,2,6,6-tetramethyl-1-piperidnyloxy, free radical) are also effective as inhibitors at low concentrations. The total amount of antioxidant plus synergists typically falls in the range of 100 to 2000 ppm relative to the weight of total base resin. Other additives, such as adhesion promoters, in types and amounts known in the art, may also be added.

These compositions will perform within the commercially acceptable range for die attach adhesives. Commercially acceptable values for die shear for the adhesives on a 80×80 mil$^2$ silicon die are in the range of greater than or equal to 1 kg at room temperature, and greater than or equal to 0.5 kg at 240° C. Acceptable values for warpage for a 500×500 mil$^2$ die are in the range of less than or equal to 70 Nm at room temperature.

In yet another embodiment of the invention, there are provided assemblies of components adhered together employing the above-described b-stageable adhesive compositions and/or die attach pastes. Thus, for example, assemblies comprising a first article permanently adhered to a second article by a cured aliquot of the above-described adhesive composition are provided. Articles contemplated for assembly employing invention compositions include memory devices, ASIC devices, microprocessors, flash memory devices, and the like. Also contemplated are assemblies comprising a microelectronic device permanently adhered to a substrate by a cured aliquot of the above-described die attach paste. Microelectronic devices contemplated for use with invention die attach pastes include copper lead frames, Alloy 42 lead frames, silicon dice, gallium arsenide dice, germanium dice, and the like.

Conditions suitable to cure invention die attach pastes include subjecting the above-described assembly to a temperature of less than about 200° C. for about 0.5 up to 2 minutes. This rapid, short duration heating can be accomplished in a variety of ways, e.g., with an in-line heated rail, a belt furnace, or the like. Optionally, the material can be oven cured at 150-220° C.

In another embodiment of the invention, there are provided methods for adhesively attaching a first article to a second article. Such methods can be performed, for example, by
(a) applying an aliquot of the adhesive composition of the invention to the first article, (b) bringing the first and second article into intimate contact to form an assembly wherein the first article and the second article are separated only by the adhesive composition applied in (a), and
(c) subjecting the assembly to conditions suitable to cure the adhesive composition.

In another embodiment of the invention, there are provided methods for adhesively attaching a semiconductor die to a substrate. Such methods can be performed, for example, by
(a) applying the b-stageable die attach paste of the invention to the substrate and/or the microelectronic device,
(b) subjecting the substrate and/or the microelectronic device to conditions suitable to form a b-staged curable film,
(c) exposing the b-staged curable film to temperature conditions suitable to melt the film,
(d) bringing the substrate and the device into intimate contact to form an assembly wherein the substrate and the device are separated only by the die-attach paste, and
(e) subjecting the b-staged curable film to conditions suitable to cure the melted film.

It is understood that using the compounds and methods of the present invention, it is possible to prepare adhesives having a wide range of cross-link density by the judicious choice and amount of polyester compounds. The greater proportion of polyfunctional compounds reacted, the greater the cross-link density. If thermoplastic properties are desired, the adhesive compositions can be prepared from (or at least contain a higher percentage of) mono-functional compounds to limit the cross-link density. A minor amount of poly-functional compounds can be added to provide some cross-linking and strength to the composition, provided the amount of poly-functional compounds is limited to an amount that does not diminish the desired thermoplastic properties. Within these parameters, the strength and elasticity of individual adhesives can be tailored to a particular end-use application.

"Cross-linking," as used herein, refers to the attachment of two or more polymer chains by bridges of an element, a molecular group, or a compound. In general, crosslinking of the compounds of the invention takes place upon heating. As cross-linking density is increased, the properties of a material can be changed from thermoplastic to thermosetting.

EXAMPLES

Example 1

The following describes an exemplary synthesis of a polyester linked acrylate or methacrylate according to the invention.

Synthesis of Compound 1

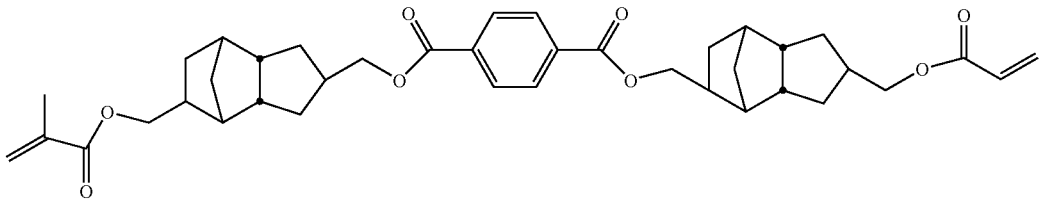

To a 500 mL round bottomed flask was added terephthalic acid (8.31 g, 50 mmol), dicyclopentadiene-dimethanol (23.6 g, 120 mmol), toluene (110 g), and methane sulfonic acid (3.5 g). This mixture was refluxed for 1.5 hours, at which time 2.0 mL of water was collected in a Dean-Stark trap. Next, acrylic acid (7.23 g, 100 mmol) and methacrylic acid (8.62 g, 100 mmol) and an additional 200 mL of toluene were added to the reaction flask. This mixture was refluxed for 2.25 hours, at which time 2.3 mL water had collected in the Dean-Stark trap. This material was then worked up with NaHCO$_3$ (25 g) and 3.5 g water followed by 21 g MgSO$_4$. Once all gas evolution had ceased, the solution was passed through silica gel and the toluene was removed by rotary evaporation, affording the product (Compound 1) (36.6 g, 95% yield).

Example 2

To a 500 mL round bottomed flask was added isophthalic acid (8.31 g, 50 mmol), dicyclopentadiene-dimethanol (23.6 g, 120 mmol), toluene (110 g), and methane sulfonic acid (3.5 g). This mixture was refluxed for 1.5 hours, at which time 2.0 mL of water was collected in a Dean-Stark trap. Next, acrylic acid (7.23 g, 100 mmol) and methacrylic acid (8.62 g, 100 mmol) and an additional 200 mL of toluene were added to the reaction flask. This mixture was refluxed for 2.5 hours, at which time 2.3 mL water had collected in the Dean-Stark trap. This material was then worked up with NaHCO$_3$ (25 g) and 3.5 g water followed by 21 g MgSO$_4$. Once all gas evolution had ceased, the solution was passed through silica gel and the toluene was removed by rotary evaporation, affording the product (Compound 2) (36.6 g, 95% yield).

Example 3

Synthesis of Compound 2

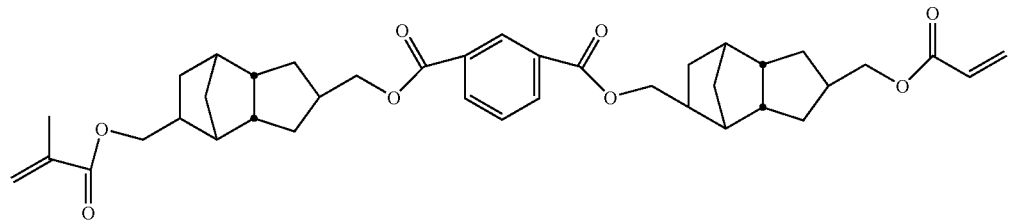

Synthesis of Compound 3

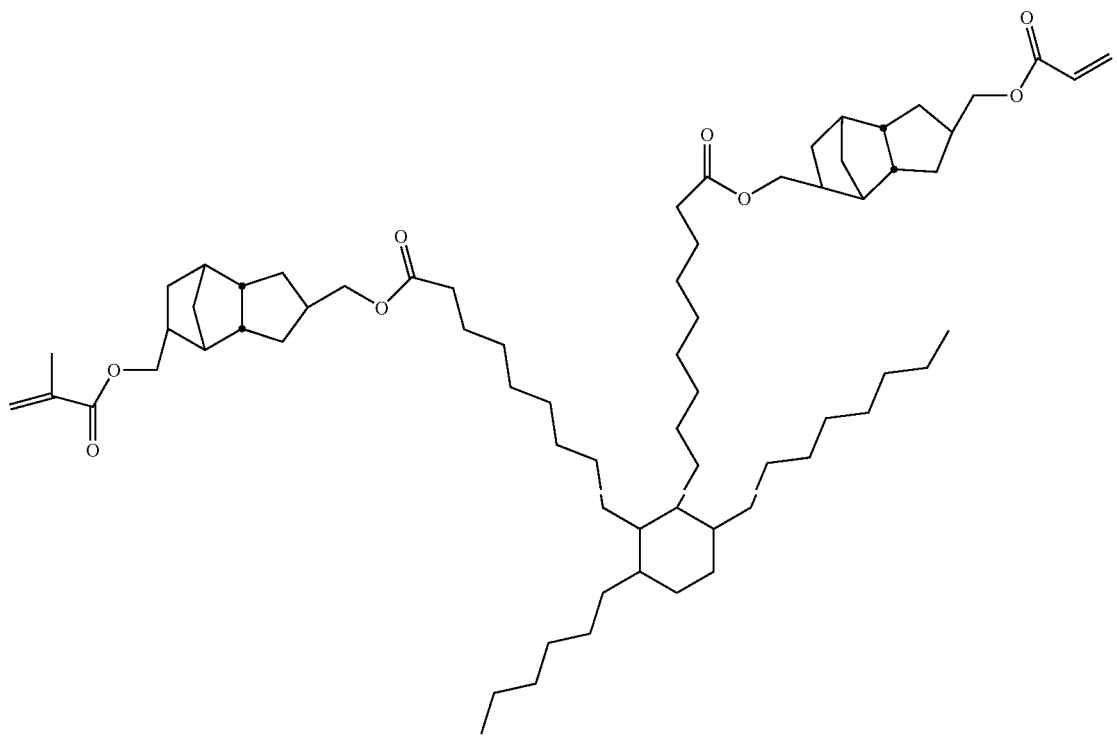

To a 500 mL round bottomed flask was added the dimmer acid Cognis Empol 1008 (28.27 g, 50 mmol), dicyclopentadiene-dimethanol (23.6 g, 120 mmol), toluene (110 g), and methane sulfonic acid (3.5 g). This mixture was refluxed for 0.5 hours, at which time 2.0 mL of water was collected in a Dean-Stark trap. Next, acrylic acid (7.23 g, 100 mmol) and methacrylic acid (8.62 g, 100 mmol) and an additional 200 mL of toluene were added to the reaction flask. This mixture was refluxed for 2.5 hours, at which time 2.1 mL water had collected in the Dean-Stark trap. This material was then worked up with NaHCO$_3$ (25 g) and 3.5 g water followed by 21 g MgSO$_4$. Once all gas evolution had ceased, the solution was passed through silica gel and the toluene was removed by rotary evaporation, affording the product (Compound 3) (54.6 g, 93% yield).

Example 4

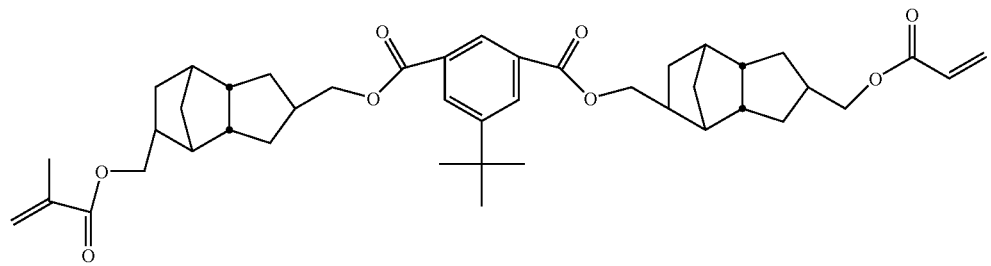

Synthesis of Compound 4

To a 500 mL round bottomed flask was added 5-t-butyl-isophthalic acid (11.2 g, 50 mmol), dicyclopentadiene-dimethanol (23.6 g, 120 mmol), toluene (110 g), and methane sulfonic acid (1.0 g). This mixture was refluxed for 2 hours, at which time 1.8 mL of water was collected in a Dean-Stark trap. Next, acrylic acid (7.23 g, 100 mmol), methacrylic acid (8.62 g, 100 mmol), methane sulfonic acid (1.5 g), and an additional 120 mL of toluene were added to the reaction flask. This mixture was refluxed for 2.5 hours, at which time 2.3 mL water had collected in the Dean-Stark trap. This material was then worked up with NaHCO$_3$ (25 g) and 3.5 g water followed by 21 g MgSO$_4$. Once all gas evolution had ceased, the solution was passed through silica gel and the toluene was removed by rotary evaporation, affording the product (Compound 4) (39.8 g, 96% yield).

While this invention has been described with respect to these specific examples, it should be clear that other modifications and variations would be possible without departing from the spirit of this invention.

What is claimed is:

1. A compound having the structure:

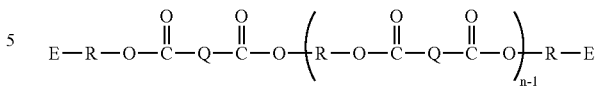

wherein:

R is substituted or unsubstituted cyclopentyl, cyclohexyl, norbornyl, tetracyclododecyl, or dicyclopentadienyl, Q is substituted or unsubstituted aliphatic, aryl, or heteroaryl;

each E is independently acrylate, methacrylate, maleimide, styrenic, vinyl ester, olefin, allyl, vinyl ether, itaconate, or fumarate; and n is 1 to 10.

2. The compound of claim 1, wherein Q is a substituted or unsubstituted aryl or heteroaryl having from 6 to 14 carbon atoms.

3. The compound of claim 1, wherein Q is a substituted or unsubstituted phenyl or naphthyl.

4. The compound of claim 1, wherein Q is a substituted or unsubstituted norbornenyl.

5. The compound of claim 1, wherein substituted aliphatic, aryl, or heteroaryl moieties comprise substituents selected from alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, amido, —C(O)H, —C(O)—, —C(O)—, —S—, —S(O)$_2$, —OC(O)—O—, —NR—C(O), —NR—C(O)—NR, —OC(O)—NR, wherein R is H or lower alkyl, acyl, oxyacyl, carboxyl, carbamate, sulfonyl, sulfonamide, or sulfuryl.

6. A compound having any one of the following structures:

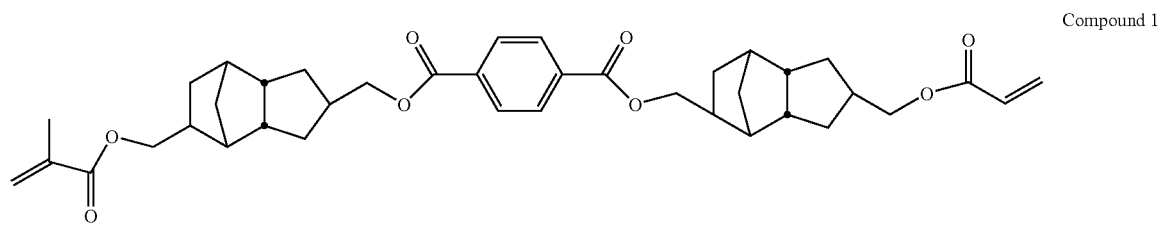
Compound 1
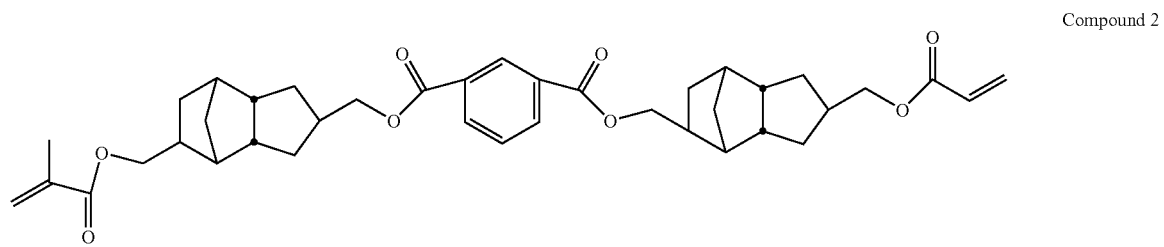
Compound 2
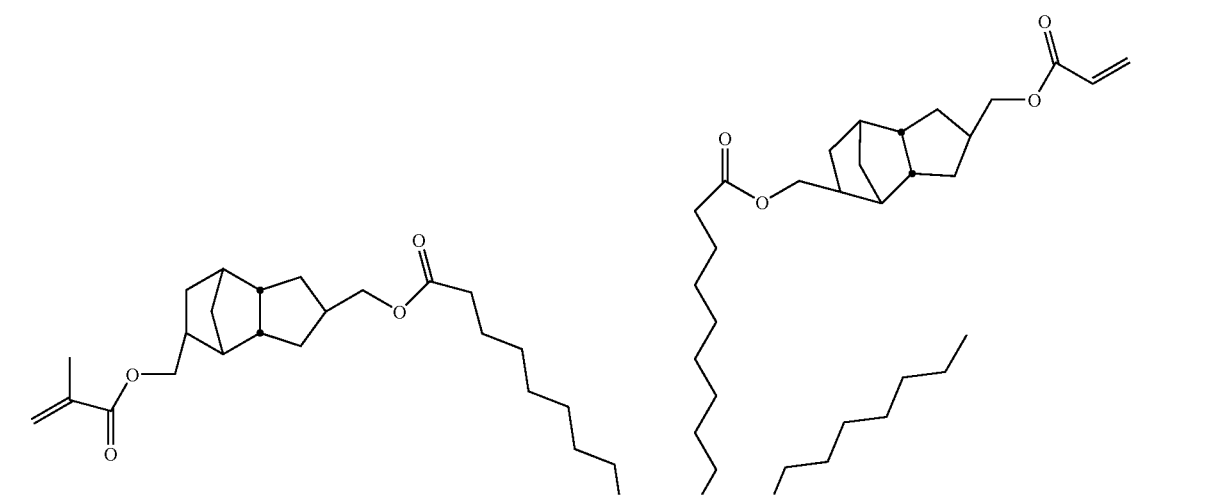
Compound 3
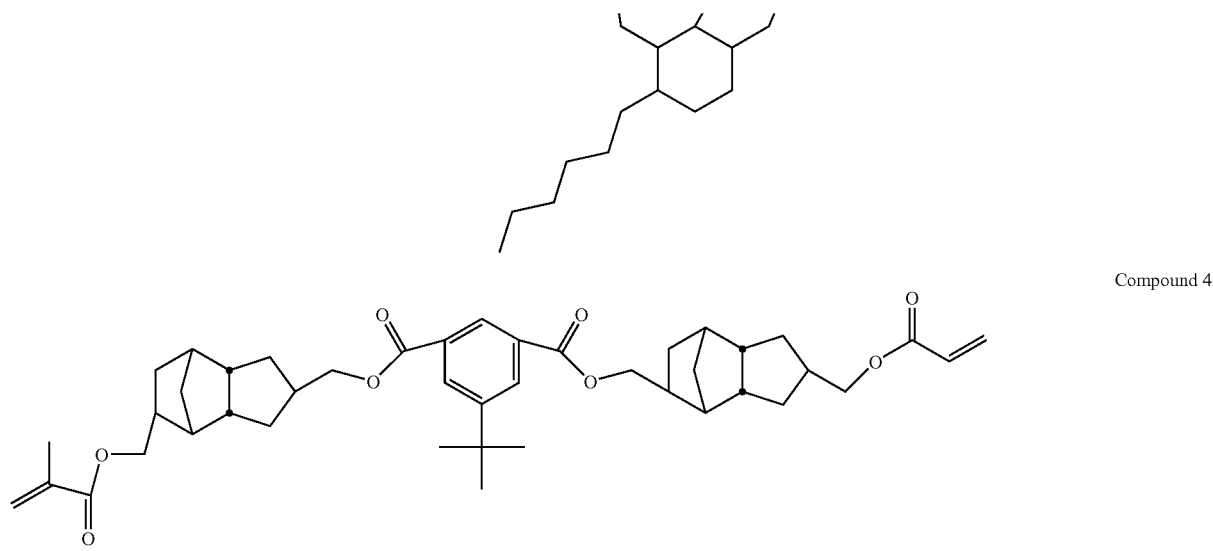
Compound 4

-continued
Compound 5
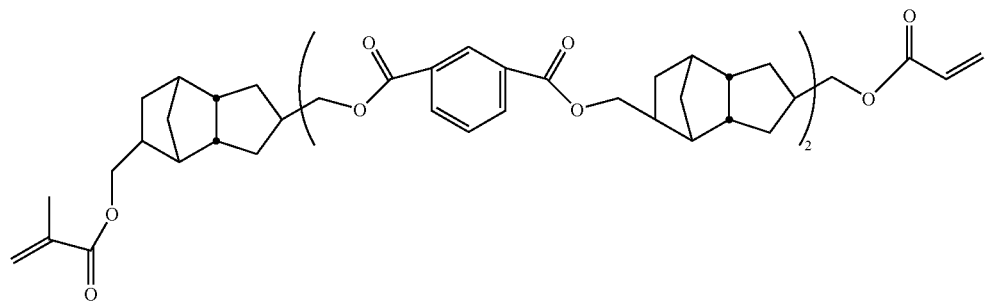
Compound 6
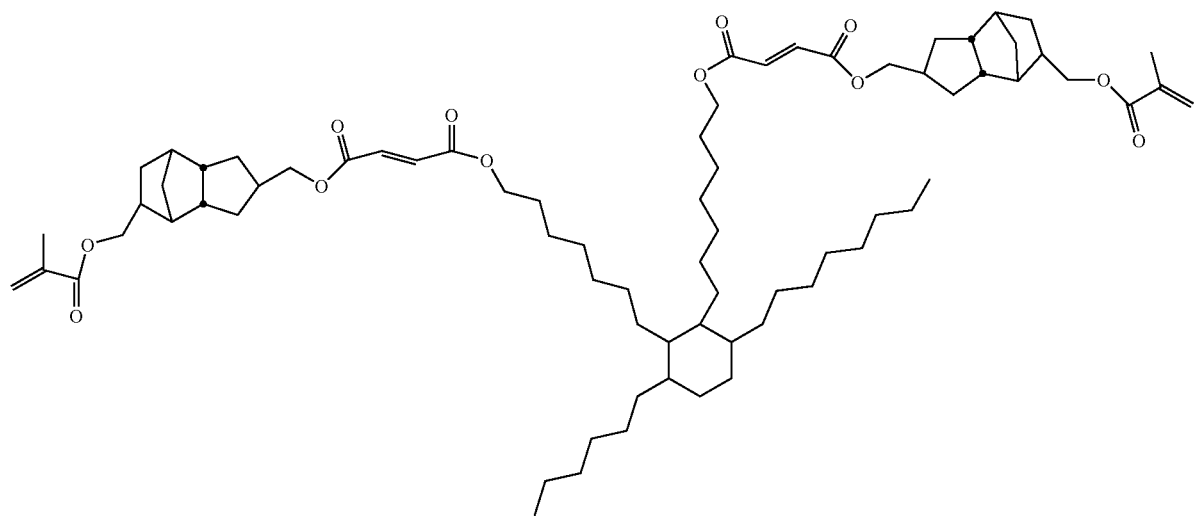
Compound 7
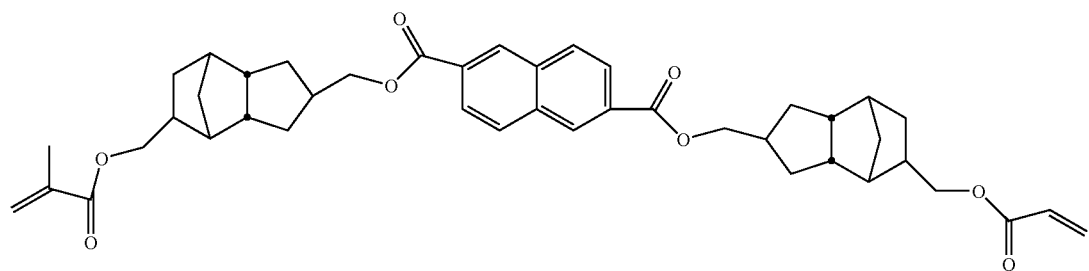
Compound 8
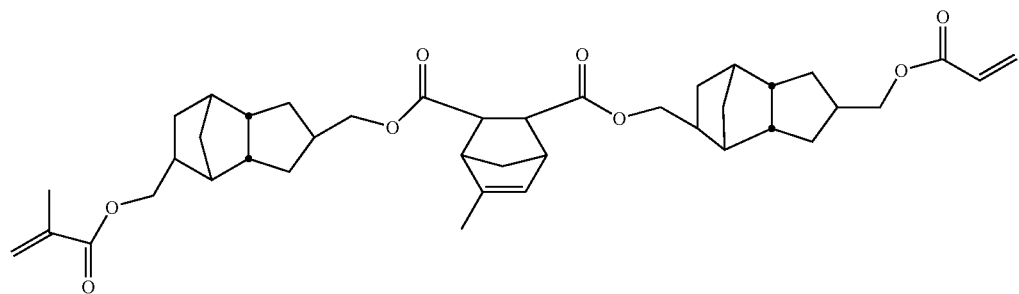

-continued
Compound 9
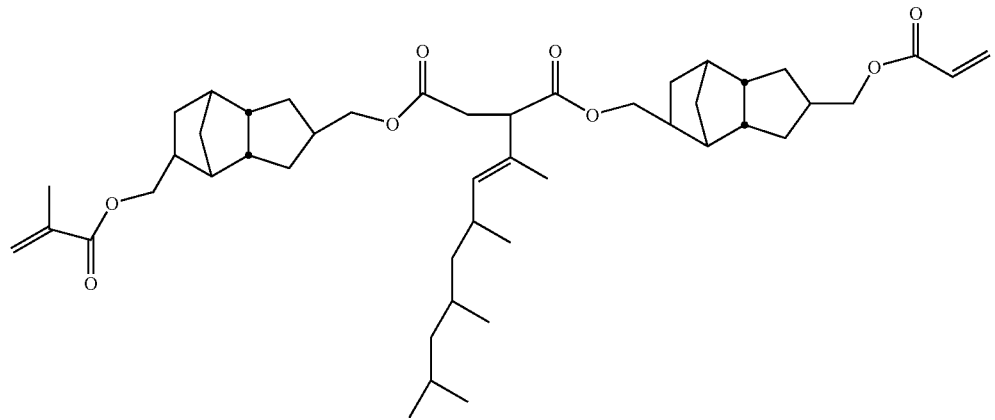
Compound 10
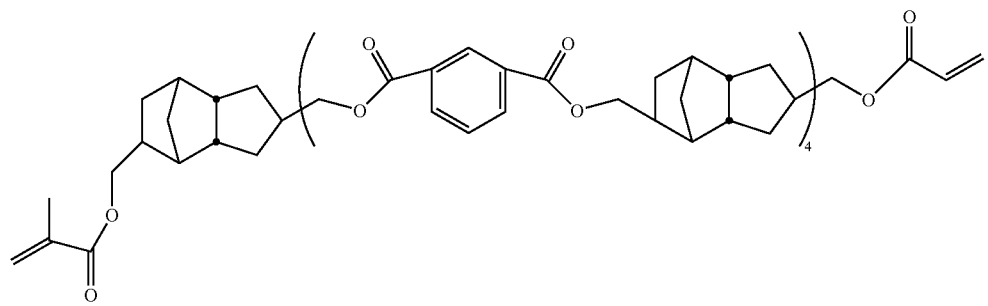
Compound 11
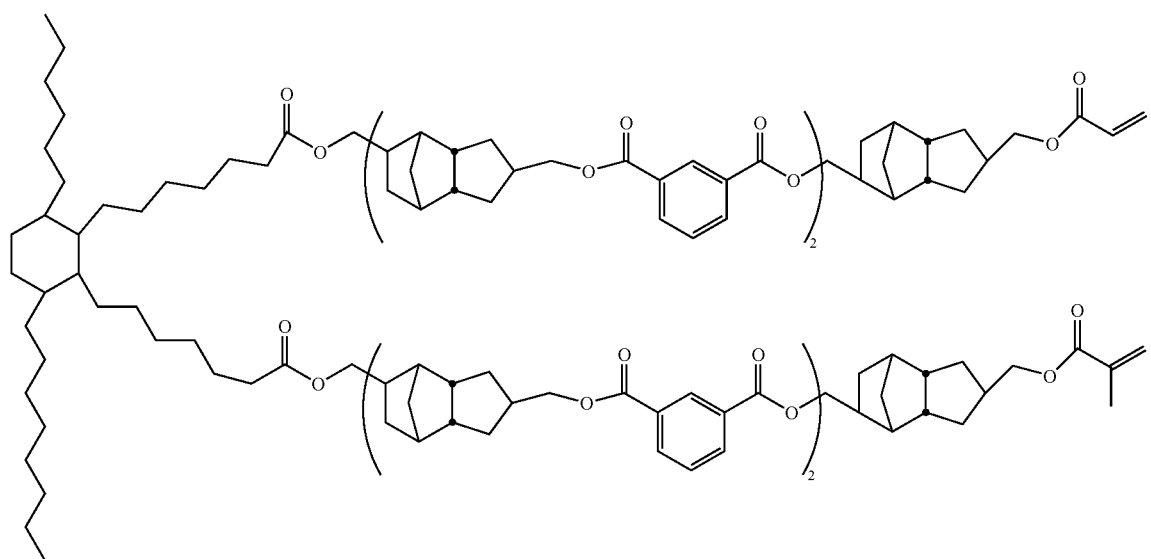

Compound 12
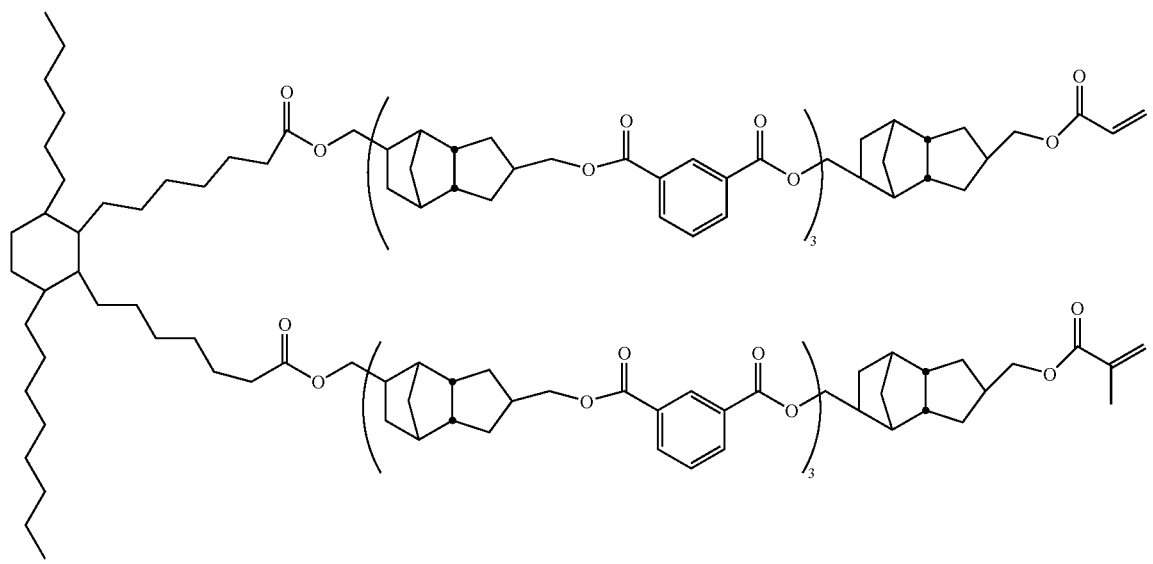
Compound 13
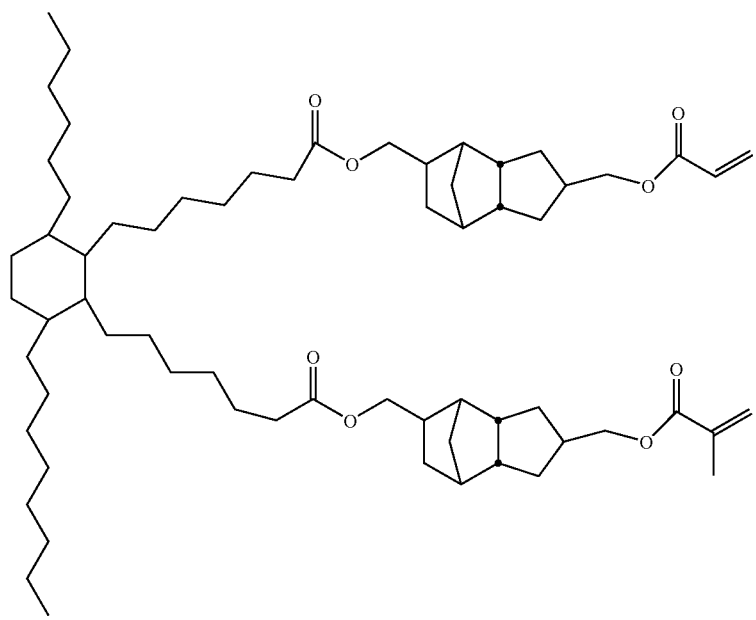
Compound 14
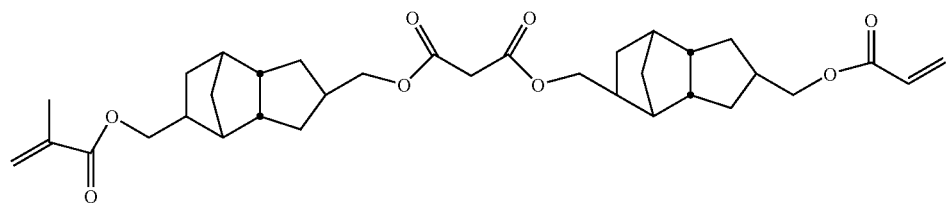
Compound 15
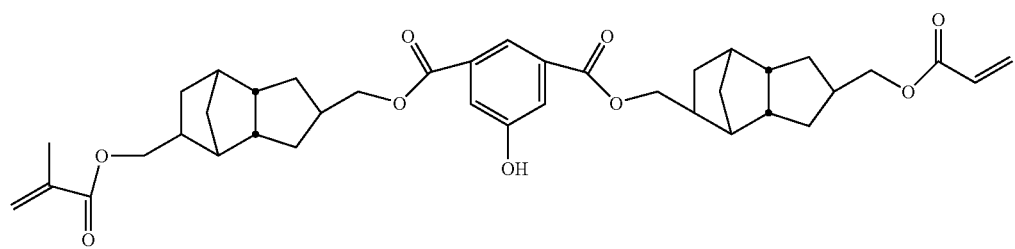

-continued
Compound 16
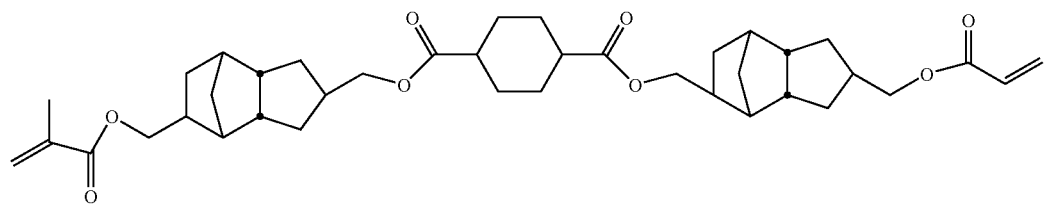
Compound 17
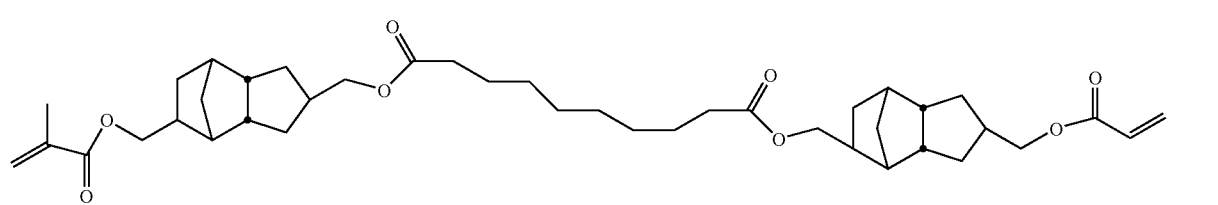
Compound 18
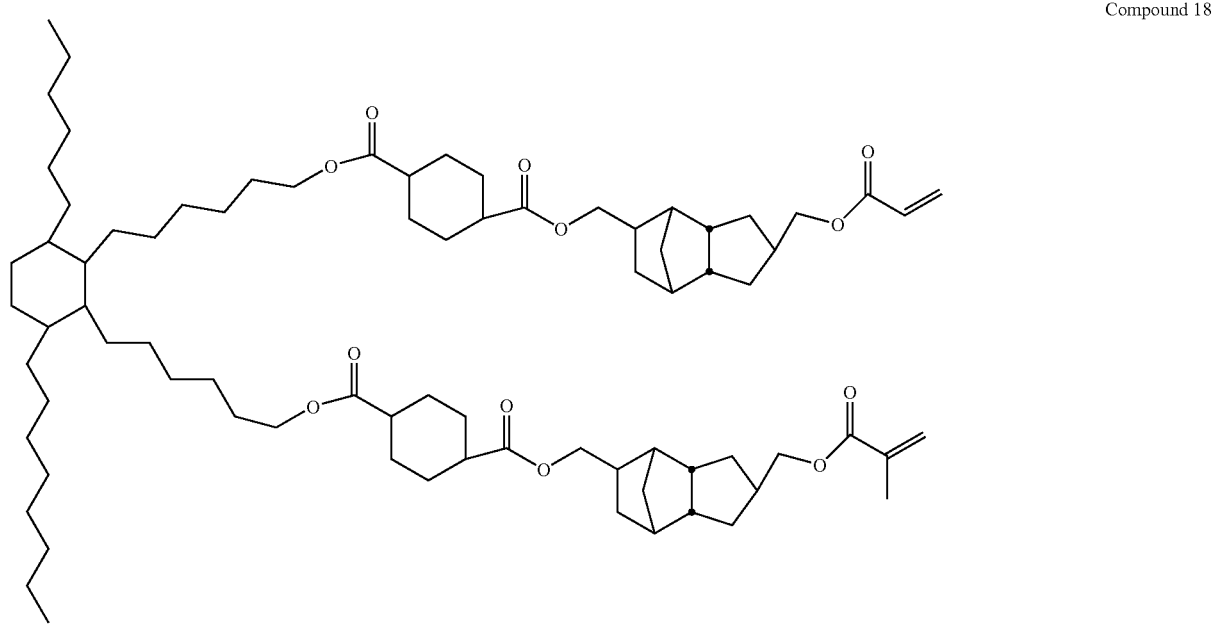
Compound 19
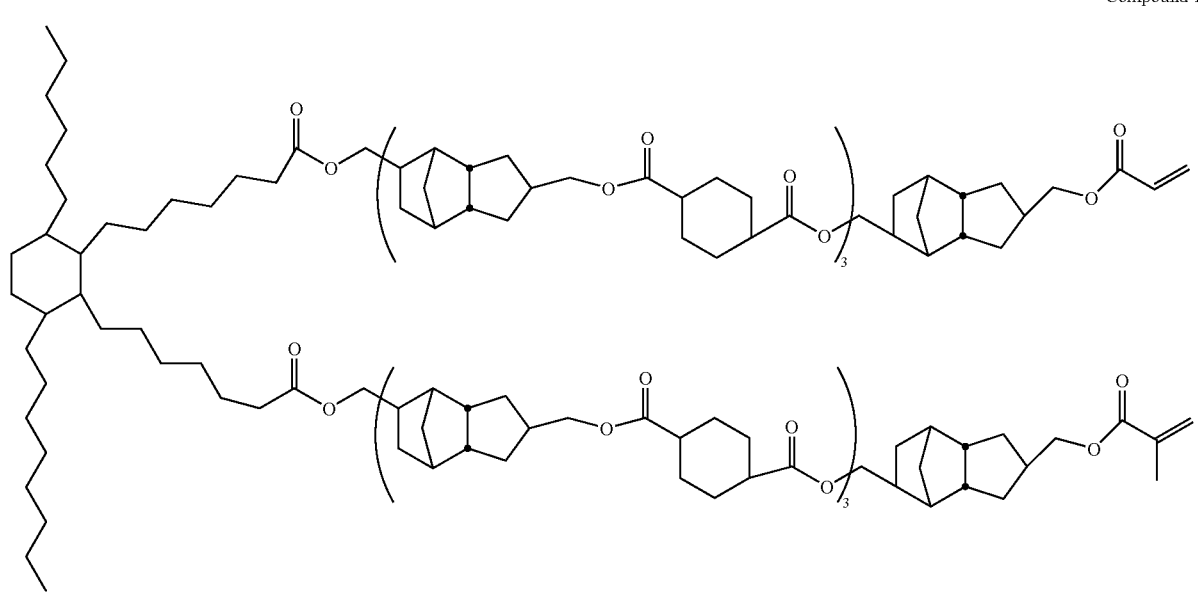

Compound 20
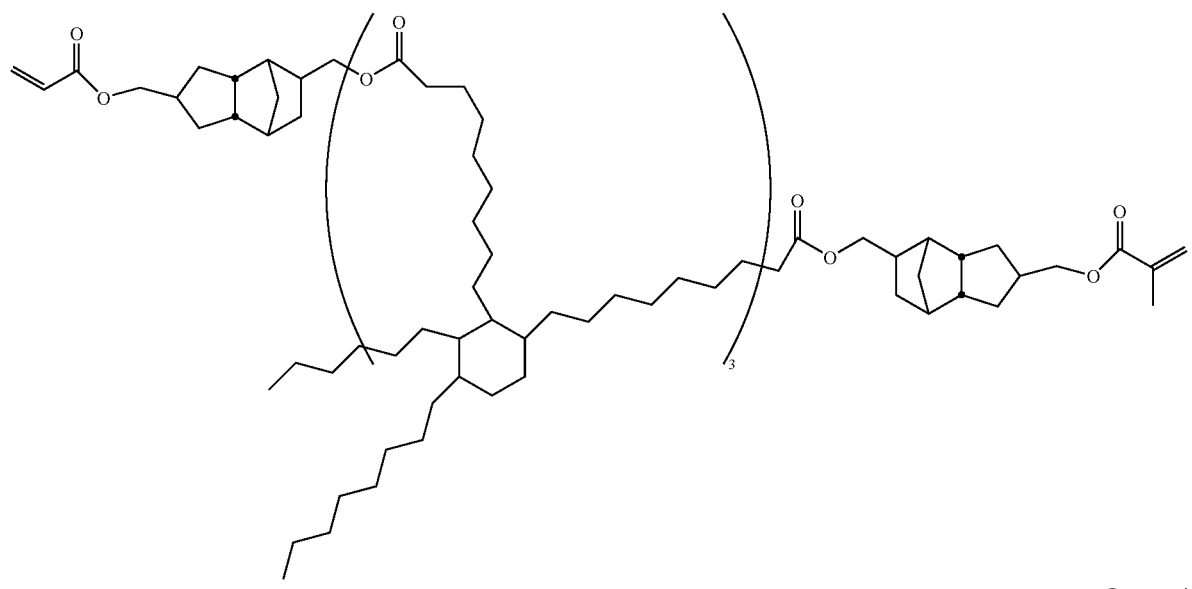
Compound 21
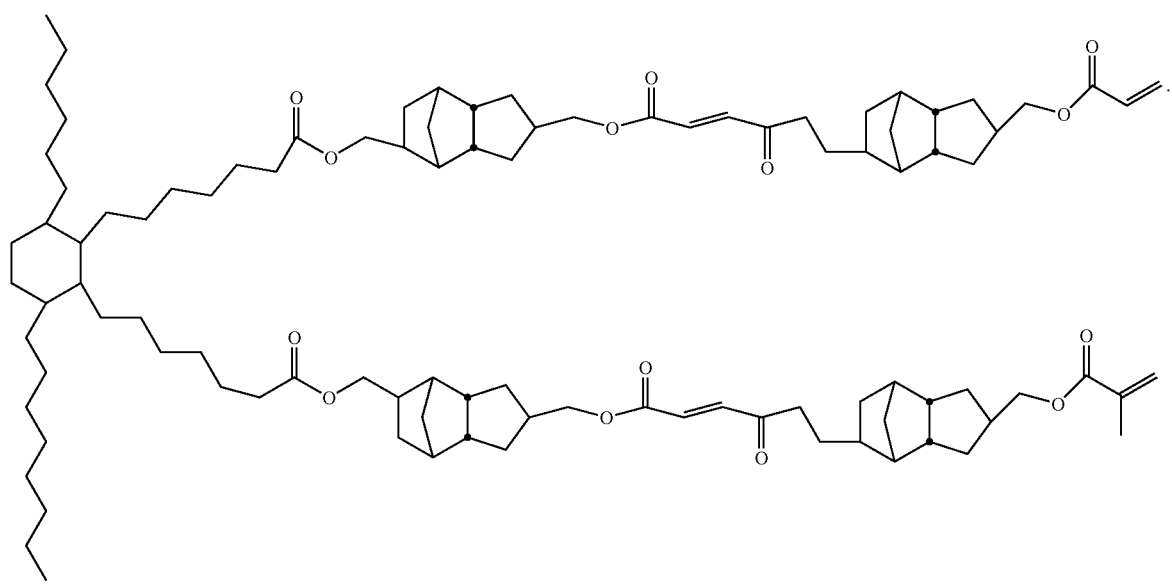
* * * * *